(12) United States Patent
Gutti

(10) Patent No.: US 11,690,666 B2
(45) Date of Patent: *Jul. 4, 2023

(54) KNIFE LOCKOUT FOR ELECTROSURGICAL FORCEPS

(71) Applicant: Covidien LP, Mansfield, MA (US)

(72) Inventor: Ravi Sekhar Gutti, Hyderabad (IN)

(73) Assignee: Covidien LP, Mansfield, MA (US)

( * ) Notice: Subject to any disclaimer, the term of this patent is extended or adjusted under 35 U.S.C. 154(b) by 596 days.

This patent is subject to a terminal disclaimer.

(21) Appl. No.: 16/853,913

(22) Filed: Apr. 21, 2020

(65) Prior Publication Data

US 2020/0246064 A1    Aug. 6, 2020

Related U.S. Application Data

(63) Continuation of application No. 15/617,283, filed on Jun. 8, 2017, now Pat. No. 10,653,475.

(51) Int. Cl.
*A61B 18/00* (2006.01)
*A61B 18/14* (2006.01)
*A61B 90/00* (2016.01)

(52) U.S. Cl.
CPC .. *A61B 18/1442* (2013.01); *A61B 2018/0063* (2013.01); *A61B 2018/00297* (2013.01);
(Continued)

(58) Field of Classification Search
CPC ........ A61B 2090/034; A61B 2090/065; A61B 2090/08021; A61B 18/1442;
(Continued)

(56) References Cited

U.S. PATENT DOCUMENTS 4,763,669 A    8/1988 Jaeger
5,100,420 A    3/1992 Green et al.
(Continued)

FOREIGN PATENT DOCUMENTS

CN    202086577 U    12/2011
CN    102525639 A    7/2012
(Continued)

OTHER PUBLICATIONS

Extended European Search Report dated Appl. No. EP 18176435.8 dated Oct. 31, 2018 (7 pages).
(Continued)

*Primary Examiner* — Michael F Peffley
*Assistant Examiner* — Nicholas S Borsch
(74) *Attorney, Agent, or Firm* — Carter, DeLuca & Farrell LLP

(57) ABSTRACT

An electrosurgical forceps includes first and second shafts configured to rotate about a pivot to move jaw members between an open position and a closed position. A knife deployment mechanism is operably coupled to a knife and is configured to move the knife between a retracted position and an extended position. A knife lockout is configured to move between a first position wherein the jaw members are in the open position and movement of the knife from the retracted position to the extended position is prevented, a second position wherein the jaw members are in the closed position and movement of the knife from the retracted position to the extended position is permitted, and a third position wherein the jaw members are in the closed position and movement of the knife from the retracted position to the extended position is prevented.

20 Claims, 11 Drawing Sheets

(52) U.S. Cl.
CPC .......... *A61B 2018/00607* (2013.01); *A61B 2018/00791* (2013.01); *A61B 2018/00875* (2013.01); *A61B 2018/00922* (2013.01); *A61B 2018/1455* (2013.01); *A61B 2090/034* (2016.02); *A61B 2090/065* (2016.02); *A61B 2090/08021* (2016.02)

(58) Field of Classification Search
CPC .......... A61B 18/1445; A61B 18/1447; A61B 2018/145; A61B 2018/1452; A61B 2018/1455; A61B 2018/1457; A61B 17/28; A61B 17/2804; A61B 2017/2808; A61B 17/2812; A61B 17/2816; A61B 17/282; A61B 17/2833; A61B 2017/2837; A61B 17/285; A61B 17/29; A61B 2017/2901; A61B 2017/2926; A61B 2017/2946; A61B 17/295
See application file for complete search history.

(56) References Cited

U.S. PATENT DOCUMENTS

| | | | |
|---|---|---|---|
| 5,258,001 A | 11/1993 | Corman | |
| 5,304,203 A | 4/1994 | El-Mallawany et al. | |
| 5,344,424 A | 9/1994 | Roberts et al. | |
| 5,540,685 A | 7/1996 | Parins et al. | |
| 5,578,052 A | 11/1996 | Koros et al. | |
| 5,611,808 A | 3/1997 | Hossain et al. | |
| 5,618,294 A | 4/1997 | Aust et al. | |
| 5,665,100 A | 9/1997 | Yoon | |
| 5,752,644 A | 5/1998 | Bolanos et al. | |
| 5,814,043 A | 9/1998 | Shapeton | |
| 5,913,874 A | 6/1999 | Berns et al. | |
| 5,960,544 A | 10/1999 | Beyers | |
| 6,050,996 A | 4/2000 | Schmaltz et al. | |
| 6,293,954 B1 | 9/2001 | Fogarty et al. | |
| 6,329,778 B1 | 12/2001 | Culp et al. | |
| 6,334,861 B1 | 1/2002 | Chandler et al. | |
| 6,406,485 B1 | 6/2002 | Hossain et al. | |
| 6,464,704 B2 | 10/2002 | Schmaltz et al. | |
| 6,511,480 B1 | 1/2003 | Tetzlaff et al. | |
| 6,673,092 B1 | 1/2004 | Bacher | |
| 7,118,570 B2 | 10/2006 | Tetzlaff et al. | |
| 7,329,257 B2 | 2/2008 | Kanehira et al. | |
| 7,431,730 B2 | 10/2008 | Viola | |
| 7,641,653 B2 | 1/2010 | Dalla Betta et al. | |
| 7,854,185 B2 | 12/2010 | Zhang et al. | |
| 7,896,878 B2 | 3/2011 | Johnson et al. | |
| 8,147,489 B2 | 4/2012 | Moses et al. | |
| 8,298,233 B2 | 10/2012 | Mueller | |
| 8,366,709 B2 | 2/2013 | Schechter et al. | |
| 8,394,096 B2 | 3/2013 | Moses et al. | |
| 8,409,246 B2 | 4/2013 | Kerr et al. | |
| 8,409,247 B2 | 4/2013 | Garrison et al. | |
| 8,425,504 B2 | 4/2013 | Orton et al. | |
| 8,425,511 B2 | 4/2013 | Olson | |
| 8,430,877 B2 | 4/2013 | Kerr et al. | |
| 8,439,913 B2 | 5/2013 | Horner et al. | |
| 8,469,716 B2 | 6/2013 | Fedotov et al. | |
| 8,469,991 B2 | 6/2013 | Kerr | |
| 8,469,992 B2 | 6/2013 | Roy et al. | |
| 10,653,475 B2 * | 5/2020 | Gutti .............. A61B 18/1442 | |
| 2011/0238067 A1 * | 9/2011 | Moses .............. A61B 18/1442 606/52 | |
| 2014/0236149 A1 | 8/2014 | Kharin et al. | |
| 2014/0243811 A1 | 8/2014 | Reschke et al. | |
| 2014/0243824 A1 | 8/2014 | Gilbert | |
| 2014/0249528 A1 | 9/2014 | Hixson et al. | |
| 2014/0250686 A1 | 9/2014 | Hempstead et al. | |
| 2014/0257274 A1 | 9/2014 | McCullough, Jr. et al. | |
| 2014/0257283 A1 | 9/2014 | Johnson et al. | |
| 2014/0257284 A1 | 9/2014 | Artale | |
| 2014/0257285 A1 | 9/2014 | Moua | |
| 2014/0276803 A1 | 9/2014 | Hart | |
| 2014/0284313 A1 | 9/2014 | Allen, IV et al. | |
| 2014/0288549 A1 | 9/2014 | Mckenna et al. | |
| 2014/0288553 A1 | 9/2014 | Johnson et al. | |
| 2014/0330308 A1 | 11/2014 | Hart et al. | |
| 2014/0336635 A1 | 11/2014 | Hart et al. | |
| 2014/0353188 A1 | 12/2014 | Reschke et al. | |
| 2015/0018816 A1 | 1/2015 | Latimer | |
| 2015/0025528 A1 | 1/2015 | Arts | |
| 2015/0032106 A1 | 1/2015 | Rachlin | |
| 2015/0051598 A1 | 2/2015 | Orszulak et al. | |
| 2015/0051640 A1 | 2/2015 | Twomey et al. | |
| 2015/0066026 A1 | 3/2015 | Hart et al. | |
| 2015/0066076 A1 | 3/2015 | Kerr et al. | |
| 2015/0080889 A1 | 3/2015 | Cunningham et al. | |
| 2015/0082928 A1 | 3/2015 | Kappus et al. | |
| 2015/0088122 A1 | 3/2015 | Jensen | |
| 2015/0088126 A1 | 3/2015 | Duffin et al. | |
| 2015/0088128 A1 | 3/2015 | Couture | |
| 2015/0094714 A1 | 4/2015 | Lee et al. | |
| 2016/0106496 A1 * | 4/2016 | Artale .............. H01J 37/263 606/171 | |
| 2016/0157924 A1 | 6/2016 | Ding et al. | |
| 2016/0157925 A1 | 6/2016 | Artale et al. | |
| 2016/0175031 A1 | 6/2016 | Boudreaux | |

FOREIGN PATENT DOCUMENTS

| | | |
|---|---|---|
| DE | 3627221 A1 | 2/1988 |
| DE | 19946527 C1 | 7/2001 |
| DE | 20121161 U1 | 4/2002 |
| DE | 202007009318 U1 | 8/2007 |
| DE | 10031773 B4 | 11/2007 |
| EP | 1281878 A1 | 2/2003 |
| EP | 2436327 A1 | 4/2012 |
| EP | 2436330 A1 | 4/2012 |
| JP | 8289895 A | 11/1996 |
| JP | 8317936 A | 12/1996 |
| JP | 09000538 A | 1/1997 |
| JP | 0010000195 A | 1/1998 |
| JP | 1147149 | 2/1999 |
| JP | 2000135222 A | 5/2000 |
| JP | 2001003400 A | 1/2001 |
| JP | 2001008944 | 1/2001 |
| JP | 2001029355 | 2/2001 |
| JP | 2001128990 A | 5/2001 |
| JP | 2001190564 A | 7/2001 |
| JP | 2002136525 A | 5/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2005312807 A | 11/2005 |
| JP | 2006015078 A | 1/2006 |
| JP | 2006501939 A | 1/2006 |
| JP | 2006095316 A | 4/2006 |
| JP | 2008054926 A | 3/2008 |
| JP | 2011125195 A | 6/2011 |
| JP | 0006030945 B2 | 11/2016 |
| SU | 401367 A1 | 10/1973 |
| WO | 9400059 A1 | 1/1994 |
| WO | 9923933 A2 | 5/1999 |
| WO | 0024330 A1 | 5/2000 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A2 | 6/2002 |
| WO | 02080786 A1 | 10/2002 |
| WO | 02080793 A1 | 10/2002 |
| WO | 2006021269 A1 | 3/2006 |
| WO | 2005110264 A2 | 4/2006 |
| WO | 2008040483 A1 | 4/2008 |
| WO | 2011018154 A1 | 2/2011 |
| WO | 2013009758 A2 | 1/2013 |

(56) References Cited

FOREIGN PATENT DOCUMENTS

| WO | 2013022928 A1 | 2/2013 | | |
|---|---|---|---|---|
| WO | 2015017991 A1 | 2/2015 | | |
| WO | WO-2015017991 A1 * | 2/2015 | ......... | A61B 18/1442 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003, pp. 87-92.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003, 1 page.
Peterson et al. "Comparison of Healing Process Following Ligation with Sutures and Bipolar Vessel Sealing" Surgical Technology International (2001). (8 pages).
"Electrosurgery: A Historical Overview" Innovations in Electrosurgery; Sales/Product Literature; Dec. 31, 2000, 6 pages.
Johnson et al. "Evaluation of a Bipolar Electrothermal Vessel Sealing Device in Hemorrhoidectomy" Sales/Product Literature; Jan. 2004, 1 page.
E. David Crawford "Evaluation of a New Vessel Sealing Device in Urologic Cancer Surgery" Sales/Product Literature 2000, 1 page.
Johnson et al. "Evaluation of the LigaSure Vessel Sealing System in Hemorrhoidectormy" American College of Surgeons (ACS) Clinicla Congress Poster (2000), 1 page.
Muller et al., "Extended Left Hemicolectomy Using the LigaSure Vessel Sealing System" Innovations That Work, Sep. 1999. (4 pages).
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002, 4 pages.
Heniford et al. "Initial Results with an Electrothermal Bipolar Vessel Sealer" Surgical Endoscopy (2000) 15:799-801. (4 pages).
Herman et al., "Laparoscopic Intestinal Resection With the LigaSure Vessel Sealing System: A Case Report"; Innovations That Work, Feb. 2002, 4 pages.
Koyle et al., "Laparoscopic Palomo Varicocele Ligation in Children and Adolescents" Pediatric Endosurgery & Innovative Techniques, vol. 6, No. 1, 2002, pp. 15-19.

W. Scott Helton, "LigaSure Vessel Sealing System: Revolutionary Hemostasis Product for General Surgery"; Sales/Product Literature 1999, 1 page.
LigaSure Vessel Sealing System, the Seal of Confidence in General, Gynecologic, Urologic, and Laparaoscopic Surgery; Sales/Product Literature; Apr. 2002, 8 pages.
Joseph Ortenberg "LigaSure System Used in Laparoscopic 1st and 2nd Stage Orchiopexy" Innovations That Work, Nov. 2002, 4 pages.
Olsson et al. "Radical Cystectomy in Females" Current Surgical Techniques in Urology, vol. 14, Issue 3, 2001, 8 pages.
Levy et al. "Randomized Trial of Suture Versus Electrosurgical Bipolar Vessel Sealing in Vaginal Hysterectomy" Obstetrics & Gynecology, vol. 102, No. 1, Jul. 2003, pp. 147-151.
"Reducing Needlestick Injuries in the Operating Room" Sales/Product Literature 2001. (1 page).
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001, 1 page.
Levy et al., "Update on Hysterectomy—New Technologies and Techniques" OBG Management, Feb. 2003, 15 pages.
Dulemba et al. "Use of a Bipolar Electrothermal Vessel Sealer in Laparoscopically Assisted Vaginal Hysterectomy" Sales/Product Literature; Jan. 2004, 1 page.
Rothenberg et al. "Use of the LigaSure Vessel Sealing System in Minimally Invasive Surgery in Children" Int'l Pediatric Endosurgery Group (IPEG) 2000, 1 page.
Craig Johnson, "Use of the LigaSure Vessel Sealing System in Bloodless Hemorrhoidectomy" Innovations That Work, Mar. 2000, 4 pages.
Levy et al. "Use of a New Energy-based Vessel Ligation Device During Vaginal Hysterectomy" Int'l Federation of Gynecology and Obstetrics (FIGO) World Congress 1999, 1 page.
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000, 1 page.
Jarrett et al., "Use of the LigaSure Vessel Sealing System for Peri-Hilar Vessels in Laparoscopic Nephrectomy" Sales/Product Literature 2000, 1 page.
McLellan et al. "Vessel Sealing for Hemostasis During Pelvic Surgery" Int'l Federation of Gynecology and Obstetrics FIGO World Congress 2000, Washington, D.C., 1 page.
McLellan et al. "Vessel Sealing for Hemostasis During Gynecologic Surgery" Sales/Product Literature 1999, 1 page.
Heniford et al. "Initial Research and Clinical Results with an Electrothermal Bipolar Vessel Sealer" Oct. 1999. (1 page).
Vallfors et al., Automatically Controlled Bipolar Electrocoagulation—"COA-COMP", Neurosurg. Rev. (1984), pp. 187-190.

* cited by examiner

KNIFE LOCKOUT FOR ELECTROSURGICAL FORCEPS

CROSS-REFERENCE TO RELATED APPLICATIONS

This application is a continuation of U.S. patent application Ser. No. 15/617,283, filed Jun. 8, 2017.

INTRODUCTION

The present disclosure relates to electrosurgical instruments and, more particularly, to electrosurgical forceps for grasping, treating, and/or dividing tissue.

BACKGROUND

A surgical forceps is a plier-like instrument which relies on mechanical action between its jaws to grasp tissue. Electrosurgical forceps utilize both mechanical clamping action and electrical energy to treat tissue, e.g., coagulate, cauterize, and/or seal tissue.

Typically, once tissue is treated, the surgeon has to accurately sever the treated tissue. Accordingly, many electrosurgical forceps have been designed which incorporate a knife configured to effectively sever tissue after treating the tissue.

SUMMARY

As used herein, the term "distal" refers to the portion that is being described which is further from a surgeon, while the term "proximal" refers to the portion that is being described which is closer to a surgeon. Further, to the extent consistent, any of the aspects described herein may be used in conjunction with any or all of the other aspects described herein.

An electrosurgical forceps provided in accordance with aspects of the present disclosure includes first and second shafts, a knife deployment mechanism disposed on one of the first or second shafts, a knife, a switch assembly, and a knife lockout. A jaw member is disposed at a distal end of each of the shafts. The shafts are configured to rotate about a pivot to move the jaw members between an open position and a closed position. The knife is operably coupled to the knife deployment mechanism and the knife deployment mechanism is configured to move the knife between a retracted position and an extended position. The switch assembly is disposed on one of the first or second shafts and is configured to be engaged by the other of the first or second shafts when the jaw members are in the closed position to move the switch assembly between a deactivated position and an activated position to control delivery of electrosurgical energy to the jaw members. The knife lockout is configured to move between a first position, a second position, and a third position. When the knife lockout is in the first position, the jaw members are in the open position and movement of the knife from the retracted position to the extended position is prevented. When the knife lockout is in the second position, the jaw members are in the closed position, the switch assembly is in the deactivated position, and movement of the knife from the retracted position to the extended position is permitted. When the knife lockout is in the third position, the jaw members are in the closed position, the switch assembly is in the activated position, and movement of the knife from the retracted position to the extended position is prevented.

In an aspect of the present disclosure, the knife lockout includes a stop configured to engage a coupling between the knife deployment mechanism and the knife to prevent movement of the knife from the retracted position to the extended position.

In another aspect of the present disclosure, the knife lockout includes a first stop and a second stop. The first stop is configured to prevent movement of the knife from the retracted position to the extended position when the knife lockout is in the first position. The second stop is spaced from the first stop and configured to prevent movement of the knife from the retracted position to the extended position when the knife lockout is in the third position.

In another aspect of the present disclosure, the knife deployment mechanism includes, a trigger extending from one of the first or second shafts, a first linkage operably coupled to the trigger, and a second linkage having a first end portion pivotably coupled to the first linkage and a second end portion pivotably coupled to the knife.

In another aspect of the present disclosure, the second end portion of the second linkage is pivotably coupled to a proximal end portion of the knife via a pivot pin, and the knife lockout is configured to engage the pivot pin to prevent movement of the knife from the retracted position to the extended position.

In another aspect of the present disclosure, the second end portion of the second linkage is pivotably coupled to a proximal end portion of the knife via a pivot pin, and the pivot pin is configured to move through a longitudinal slot defined along one of the first or second shafts upon movement of the knife between the retracted and extended positions.

In another aspect of the present disclosure, the knife lockout includes a flexible cantilever arm having a finger extending perpendicularly from a free end thereof. The finger is configured to be engaged by one of the first or second shafts to flex the cantilever arm to move the knife lockout between the first, second, and third positions.

In another aspect of the present disclosure, the knife lockout is configured to facilitate movement of the knife from the extended position to the retracted position upon movement of the knife lockout toward the first position.

In another aspect of the present disclosure, the electrosurgical forceps includes a biasing spring operably coupled to the knife deployment mechanism and configured to bias the knife toward the retracted position.

In another aspect of the present disclosure, at least one of the jaw members includes a knife channel extending at least partially therethrough and configured to receive the knife upon movement of the knife from the retracted position to the extended position.

In another aspect of the present disclosure, at least one of the jaw members includes an electrically conductive sealing surface adapted to electrically connect to a source of electrosurgical energy.

In accordance with other embodiments of the present disclosure, an electrosurgical forceps includes first and second shafts, a knife deployment mechanism disposed on one of the first or second shafts, a knife, and a knife lockout. A jaw member is disposed at a distal end of each of the first and second shafts. The shafts are configured to rotate about a pivot to move the jaw members between an open position and a closed position. The knife is operably coupled to the knife deployment mechanism and the knife deployment mechanism is configured to move the knife between a retracted position and an extended position. The knife lockout is configured to move between a first position, a second position, and a third position. When the knife lockout is in the first position, the jaw members are in the open position and movement of the knife from the retracted position to the extended position is prevented. When the knife lockout is in the second position, the jaw members are in the closed position and movement of the knife from the retracted position to the extended position is permitted. When the knife lockout is in the third position, the jaw members are in the closed position and movement of the knife from the retracted position to the extended position is prevented.

In an aspect of the present disclosure, the electrosurgical forceps includes a switch assembly disposed on one of the first or second shafts and configured to be engaged by the other of the first or second shafts when the jaw members are in the closed position to move the switch assembly between a deactivated position and an activated position to control delivery of electrosurgical energy to the jaw members.

In an aspect of the present disclosure, the switch assembly is in the deactivated position when the knife lockout is in the second position and in the activated position when the knife lockout is in the third position.

In an aspect of the present disclosure, the knife lockout includes a first stop and a second stop. The first stop is configured to prevent movement of the knife from the retracted position to the extended position when the knife lockout is in the first position. The second stop is spaced from the first stop and is configured to prevent movement of the knife from the retracted position to the extended position when the knife lockout is in the third position.

In an aspect of the present disclosure, the knife deployment mechanism includes a trigger extending from one of the first or second shafts, a first linkage operably coupled to the trigger, and a second linkage having a first end portion pivotably coupled to the first linkage and a second end portion pivotably coupled to the knife.

In an aspect of the present disclosure, the second end portion of the second linkage is pivotably coupled to a proximal end portion of the knife via a pivot pin, and the knife lockout is configured to engage the pivot pin to prevent movement of the knife from the retracted position to the extended position.

In an aspect of the present disclosure, the knife lockout is configured to facilitate movement of the knife from the extended position to the retracted position upon movement of the knife lockout toward the first position.

In an aspect of the present disclosure, the electrosurgical forceps includes a biasing spring operably coupled to the knife deployment mechanism and configured to bias the knife toward the retracted position.

In accordance with yet other embodiments of the present disclosure, an electrosurgical forceps includes first and second shafts, a knife deployment mechanism disposed on one of the first or second shafts, a knife operably coupled to the knife deployment mechanism, a switch assembly, and a knife lockout. A jaw member is disposed at a distal end of each of the first and second shafts. The shafts are configured to rotate about a pivot to move the jaw members between an open position and a closed position. The knife deployment mechanism is configured to move the knife between a retracted position and an extended position. The switch assembly is disposed on one of the first or second shafts and is configured to be engaged by the other of the first or second shafts when the jaw members are in the closed position to move the switch assembly between a deactivated position and an activated position to control delivery of electrosurgical energy to the jaw members. The knife lockout includes a first stop and a second stop spaced from the first stop. The knife lockout is configured to move between a first position, a second position and a third position. When the knife lockout is in the first position, the jaw members are in the open position and the first stop prevents movement of the knife from the retracted position to the extended position. When the knife lockout is in the second position, the jaw members are in the closed position, the switch assembly is in the deactivated position, and movement of the knife from the retracted position to the extended position is permitted. When the knife lockout is in the third position, the jaw members are in the closed position, the switch assembly is in the activated position, and the second stop prevents movement of the knife from the retracted position to the extended position.

BRIEF DESCRIPTION OF THE DRAWINGS

Various aspects and features of the present electrosurgical forceps are described hereinbelow with reference to the drawings wherein like numerals designate identical or corresponding elements in each of the several views.

DETAILED DESCRIPTION

The present disclosure describes electrosurgical forceps for grasping, treating, and/or dividing tissue. The forceps includes two shafts each having a jaw member disposed at a distal end thereof and movable between open and closed positions to grasp tissue. The electrosurgical forceps also includes a knife configured to divide grasped tissue following treatment of the tissue (e.g., a tissue seal cycle). A knife lockout works in conjunction with the shafts to prevent deployment of the knife prior to the shafts reaching a sufficiently-approximated position corresponding to a sufficiently-closed position of jaw members as well as to prevent deployment of the knife during treatment of tissue.

Figure 1:
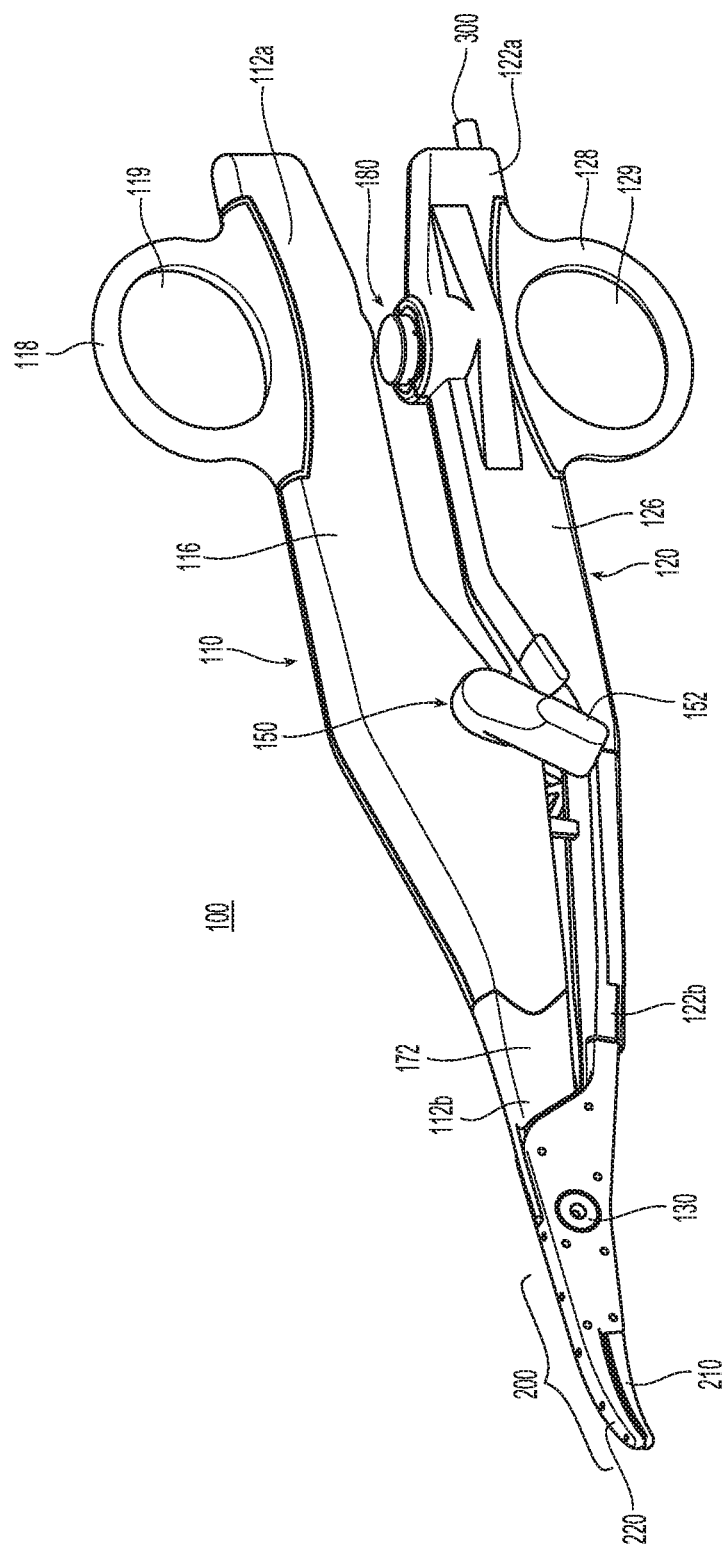
FIG. 1 is a side, perspective view of an electrosurgical forceps provided in accordance with aspects of the present disclosure.
Figure 2A:
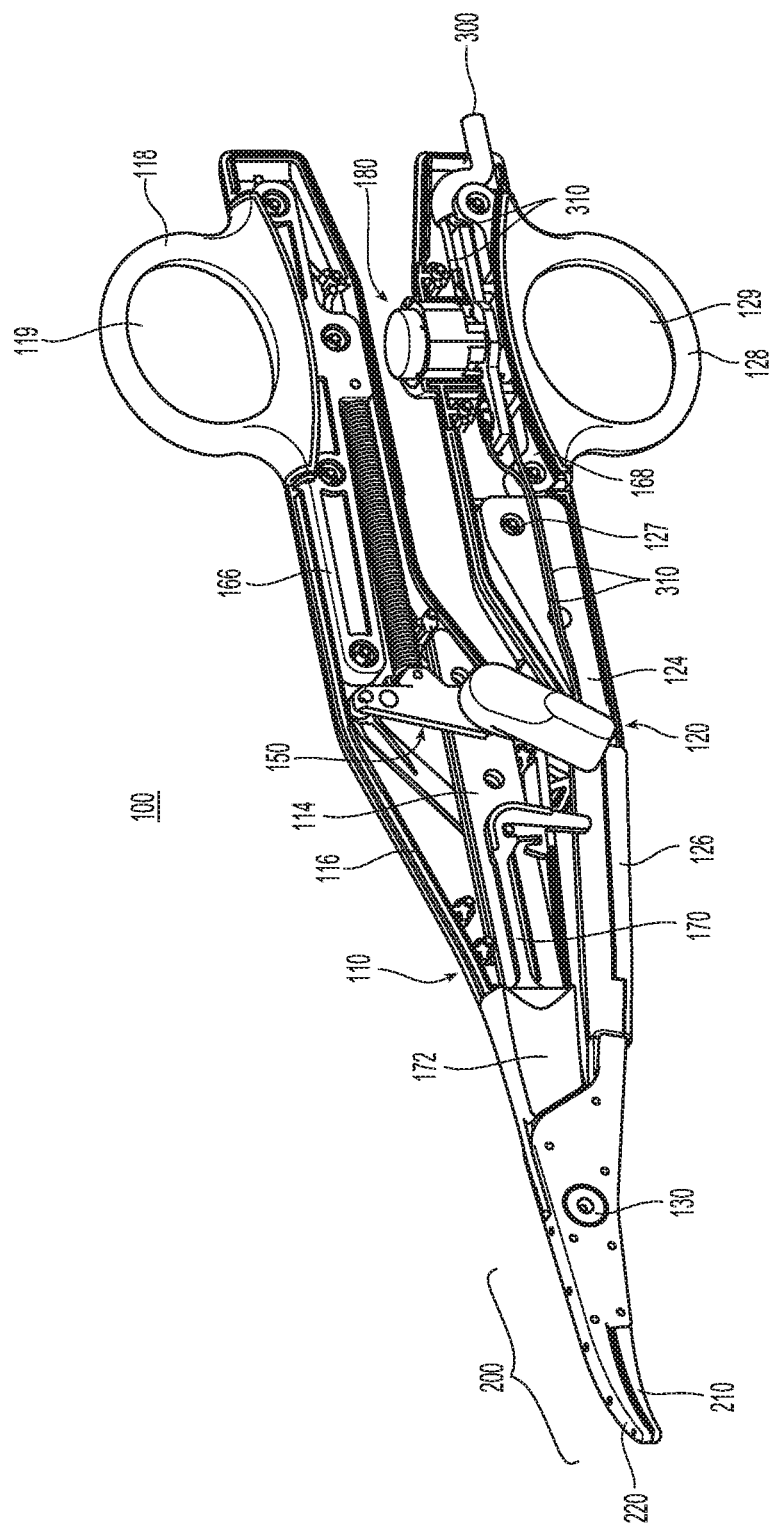
FIG. 2A is a perspective view from one side of the forceps of FIG. 1 with portions of outer housings of first and second shafts removed to illustrate the internal components therein.
Figure 2B:
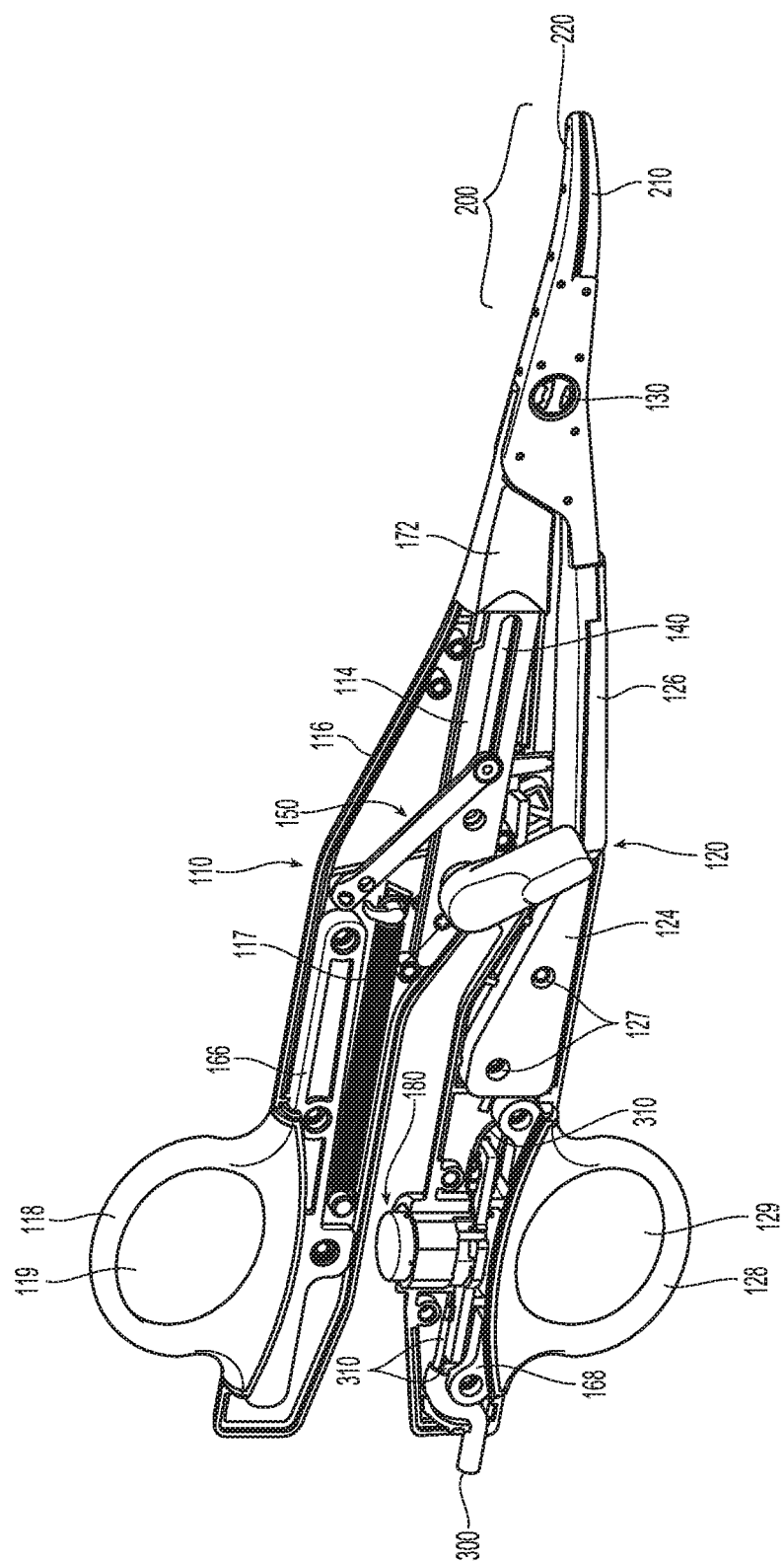
FIG. 2B is a perspective view from the other side of the forceps of FIG. 1 with other portions of the outer housings of the shafts removed to illustrate the internal components therein.

Referring generally to FIGS. 1-2B, a forceps 100 provided in accordance with the present disclosure includes first and second shafts 110, 120 each having a proximal end portion 112a, 122a and a distal end portion 112b, 122b. An end effector assembly 200 of forceps 100 includes first and second jaw members 210, 220 extending from distal end portions 112b, 122b of shafts 110, 120, respectively. Forceps 100 further includes a pivot member 130 pivotably coupling first and second shafts 110, 120 with one another, a knife 140 (FIGS. 9-10), a knife deployment mechanism 150 for selectively deploying knife 140 relative to end effector assembly 200, a knife lockout 170 (FIGS. 11A-11C) for preventing deployment of knife 140 prior to sufficient closure of jaw members 210, 220, and a switch assembly 180 including a depressible activation button 183b for enabling the selective supply of electrosurgical energy to end effector assembly 100. An electrosurgical cable 300 electrically couples forceps 100 to a source of energy (not shown), e.g., an electrosurgical generator, to enable the supply of electrosurgical energy to jaw members 210, 220 of end effector assembly 200 upon activation of switch assembly 180.

Continuing with reference to FIGS. 1-2B, each shaft 110, 120 includes an inner frame 114, 124, an outer housing 116, 126 surrounding at least a portion of the respective inner frame 114, 124, and a handle 118, 128 engaged with the respective outer housing 116, 126 towards proximal end portions 112a, 122a of shafts 110, 120, respectively. Inner frames 114, 124 are described in greater detail below. Outer housings 116, 126 enclose and/or operably support the internal components disposed within shafts 110, 120. More specifically, as detailed below, outer housing 116 of shaft 110 encloses and supports at least a portion of inner frame 114, knife deployment mechanism 150, and lockout 170, while outer housing 126 of shaft 120 receives electrosurgical cable 300 and encloses and supports at least a portion of inner frame 124, switch assembly 180, and the lead wires 310 of electrosurgical cable 300. Handles 118, 128 are engaged with outer housings 116, 126 towards proximal end portions 112a, 112b of shafts 110, 120 and extend outwardly from shafts 110, 120. Handles 118, 128 define finger holes 119, 129 configured to facilitate grasping and manipulation of shafts 110, 120.

Figure 3A:
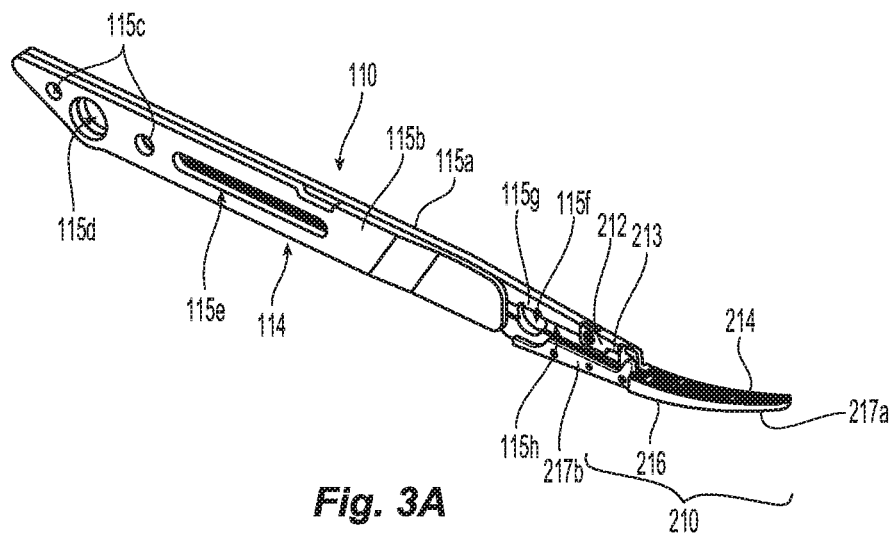
FIG. 3A is a perspective view of an inner frame and a jaw member of the first shaft of the forceps of FIG. 1.

Referring to FIG. 3A, inner frame 114 of shaft 110 includes a body plate 115a and a reinforcing plate 115b attached to body plate 115a, e.g., via welding, to provide increased lateral stiffness and structural support thereto. In embodiments, reinforcing plate 115b may be welded to body plate 115a in at least two places, e.g., towards the proximal and distal end portions thereof. The increased lateral stiffness provided by reinforcing plate 115b helps ensure alignment of a depressible button 183b (FIG. 12A) of switch assembly 180 with outer housing 116 of shaft 110 (FIG. 1) such that depressible button 183b is depressed and switch assembly 180 activated upon sufficient approximation of shafts 110, 120. While switch assembly 180 is shown in the illustrated embodiments as supported by outer housing 126 of shaft 120, it is also contemplated that switch assembly 180 may be supported by outer housing 116 of shaft 110.

Inner frame 114 defines one or more location apertures 115c, a trigger aperture 115d, and a longitudinal slot 115e that extends through both body plate 115a and reinforcing plate 115b. The one or more location apertures 115c are configured to receive corresponding posts 117 of outer housing 116 to locate and maintain inner frame 114 in position within outer housing 116. Body plate 115a extends distally beyond reinforcing plate 115b to enable attachment of jaw support 212 of jaw member 210 thereto, e.g., via staking or other suitable engagement. The portion of body plate 115a that extends distally beyond reinforcing plate 115b further defines a pivot aperture 115f extending transversely therethrough. A stop protrusion 115g extends from inner frame 114 into pivot aperture 115f, as detailed below. Body plate 115a of inner frame 114 further defines a longitudinal channel 115h oriented towards reinforcing plate 115b such that reinforcing plate 115b encloses a portion of longitudinal channel 115h.

Figure 3B:
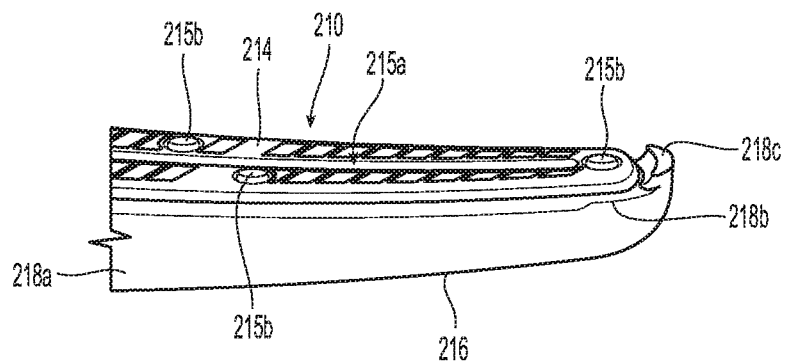
FIG. 3B is an enlarged, side, perspective view of a distal portion of the jaw member of FIG. 3A.

With additional reference to FIG. 3B, as noted above, jaw support 212 of jaw member 210 is staked or otherwise engaged, e.g., welded, press-fit, mechanically locked, etc., to the portion of body plate 115a that extends distally beyond reinforcing plate 115b. Jaw member 210 further includes an electrically-conductive, tissue-contacting surface 214 and an insulative housing 216. Tissue-contacting surface 214 defines a longitudinally-extending knife channel 215a extending at least partially therethrough. Tissue-contacting surface 214 may include one or more stop members 215b disposed on and electrically isolated from the tissue-contacting surface 214. Insulative housing 216 of jaw member 210 is overmolded or otherwise secured about a portion of jaw support 212, tissue-contacting surface 214, and body plate 115a of inner frame 114 of shaft 110. Insulative housing 216 includes a distal portion 217a and a proximal extension portion 217b. Proximal extension portion 217b of insulative housing 216 is configured to extend proximally along body plate 115a of inner frame 114 to (or proximally beyond) pivot aperture 115f of body plate 115a. The electrical lead 310 (FIGS. 2A and 2B) is configured to electrically couple to tissue-contacting surface 214 and is captured between body plate 115a and proximal extension portion 217b of insulative housing 216 to protect and facilitate routing of the electrical lead 310 from shaft 120, around pivot aperture 115f, and distally therefrom to electrically couple to tissue-contacting surface 214.

Distal portion 217a of insulative housing 216 of jaw member 210 extends about the periphery of tissue-contacting surface 214 and defines a main section 218a, a raised section 218b, and a beak section 218c. Main section 218a of distal portion 217a of insulative housing 216 extends on either side of tissue-contacting surface 214 and is offset relative thereto such that tissue-contacting surface 214 is raised relative to main section 218a. Raised section 218b of distal portion 217a of insulative housing 216 extends distally from main section 218a on either side of tissue-contacting surface 214 and is still recessed relative to tissue-contacting surface 214 but is closer to being co-planar with tissue-contacting surface 214 as compared to main section 218a. Beak section 218c of distal portion 217a of insulative housing 216 is disposed distally of tissue-contacting surface 214 and extends to or beyond tissue-contacting surface 214. Beak section 218c inhibits tissue from entering the area between jaw members 210, 220 of end effector assembly 200 when end effector assembly 200 is disposed in the closed position and utilized for blunt dissection (see FIG. 5A).

Figure 4A:
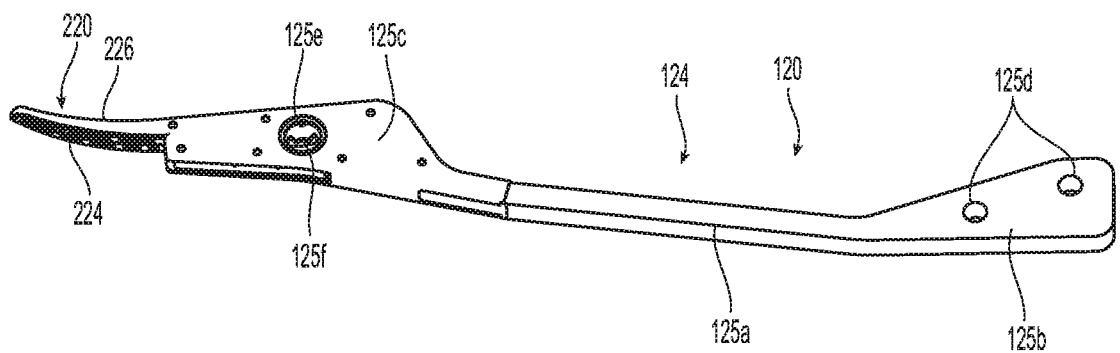
FIG. 4A is a perspective view of an inner frame and a jaw member of the second shaft of the forceps of FIG. 1.

Turning to FIG. 4A, inner frame 124 of shaft 120 includes an elongated body portion 125a, an enlarged proximal portion 125b, and a distal clevis portion 125c. Enlarged proximal portion 125b of inner frame 124 provides additional structural support to shaft 120 and defines one or more location apertures 125d that, similarly as with location apertures 115c of inner frame 114 of shaft 110 (FIG. 3A), are configured to receive corresponding posts 127 of outer housing 126 to locate and maintain inner frame 124 in position within outer housing 126. Elongated body portion 125a of inner frame 124 extends through outer housing 126 of shaft 120, while distal clevis portion 125c of shaft 120 extends distally from outer housing 126. Distal clevis portion 125c may be welded to, monolithically formed with, or otherwise engaged to elongated body portion 125a of inner frame 124. Distal clevis portion 125c of inner frame 124 is detailed below.

Figure 4B:
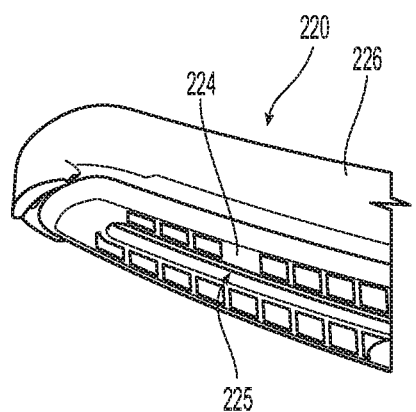
FIG. 4B is an enlarged, perspective view of a distal portion of the jaw member of FIG. 4A.

Elongated body portion 125a defines a flexibility that enables flexure of elongated body portion 125a in response to application of a jaw force at jaw member 220. The flexibility or stiffness of elongated body portion 125a is defined by a spring constant (e.g., a spring constant of about 0.404 lbf/in). This configuration enables the application of a jaw force within a particular range, e.g., between about 3 $kg/cm^2$ and about 16 $kg/cm^2$, when shafts 110, 120 are disposed in the approximated position corresponding to a closed position of jaw members 210, 220 (See FIGS. 1-2B). Referring also to FIGS. 3A, 3B, and 4B, in embodiments, in addition to the flexion of elongated body portion 125a providing a jaw force within a particular range, flexion of the jaw members 210, 220 may also contribute to providing a jaw force within a particular range. More specifically, due to the relatively fine configuration of the jaw members 210, 220 and the fact that the jaw members 210, 220 taper in height and width from the proximal ends to the distal ends thereof, the jaw members 210, 220 themselves provide flexibility that, in conjunction with the flexibility of elongated body portion 125a, provide a jaw force within a particular range to facilitate tissue treatment.

Referring to FIGS. 4A and 4B, jaw member 220 of end effector assembly 200 is supported on a distal extension (not shown) of distal clevis portion 125c of inner frame 124 of shaft 120. The distal extension (not shown) of distal clevis portion 125c of inner frame 124 serves as the jaw frame of jaw member 220. Jaw member 220 further includes an electrically-conductive, tissue-contacting surface 224 and an insulative housing 226. Tissue-contacting surface 224 defines a longitudinally-extending knife channel 225 extending at least partially therethrough and may include one or more stop members, similarly as with jaw member 210 (FIG. 3B). Insulative housing 226 of jaw member 220 is similar to that of jaw member 210 (FIG. 3B) and, thus, the features thereof will not be repeated here.

As illustrated in FIGS. 1 and 3A-4B, jaw members 210, 220 taper in height and width from the proximal ends to the distal ends thereof, thus facilitating blunt dissection and inhibiting jaw splay. Jaw members 210, 220 also define curved configurations that facilitate visualization of the surgical site and provide increased surface area for grasping tissue.

Figure 5A:
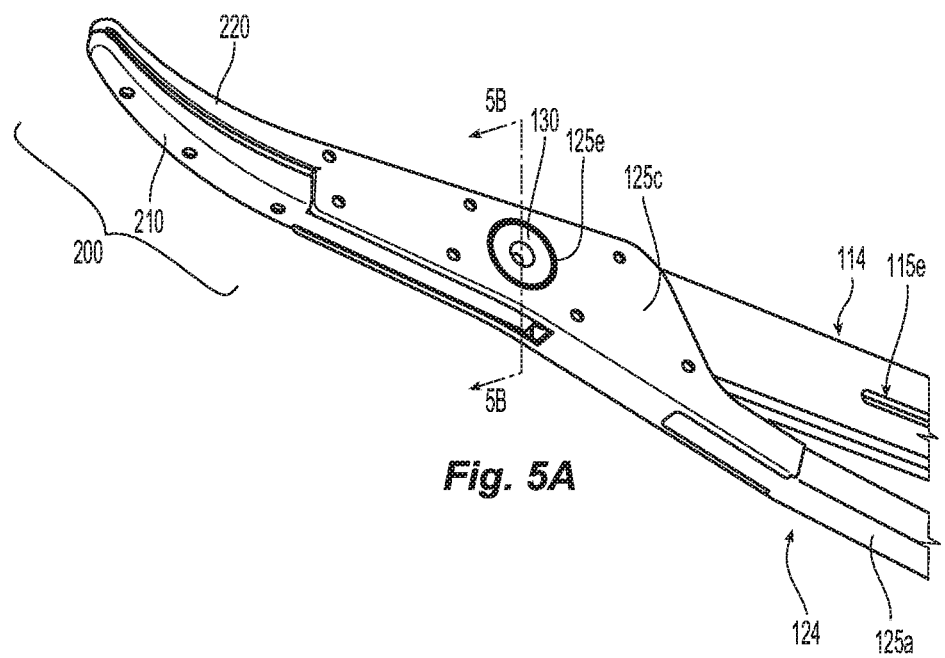
FIG. 5A is a perspective view of a distal portion of the forceps of FIG. 1 illustrating the first and second jaw members pivotably coupled to form the end effector assembly.
Figure 5B:
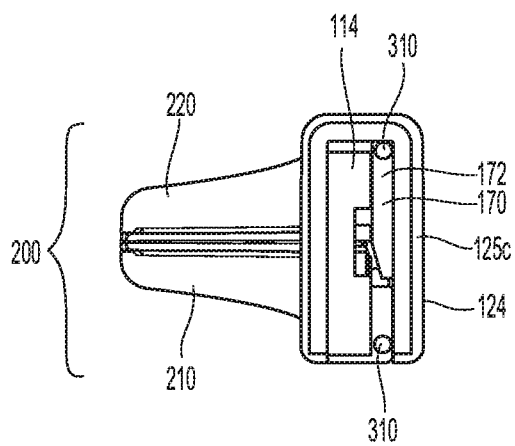
FIG. 5B is a transverse, cross-sectional view taken along section line "5B-5B" in FIG. 5A.

With reference to FIGS. 5A-5B, distal clevis portion 125c of inner frame 124 of shaft 120 and body plate 115a of inner frame 114 of shaft 110 are pivotably coupled to one another via pivot member 130 such that shafts 110, 120 are movable relative to one another between spaced-apart and approximated positions to thereby pivot jaw members 210, 220 relative to one another between open and closed positions. More specifically, distal clevis portion 125c and body plate 115a define a lock-box configuration wherein distal clevis portion 125c includes a bifurcated, U-shaped configuration having an elongated slot defined therein, and wherein body plate 115a is configured for nested receipt within the elongated slot of the bifurcated, U-shaped distal clevis portion 125c. Referring in particular to FIG. 5B, sufficient clearance is provided between distal clevis portion 125c and body plate 115a when body plate 115a is nested within distal clevis portion 125c such that lead wires 310 are permitted to extend therethrough, ultimately to electrically couple tissue-contacting surfaces 214, 224 (FIGS. 3B and 4B, respectively) to switch assembly 180 (FIGS. 1-2B) and the source of energy (not shown). Further, body 172 of knife lockout 170 is configured for positioning adjacent body plate 115a within distal clevis portion 125c to minimize lateral play between body plate 115a and distal clevis portion 125c and to act as a wire guide to maintain the lead wires 310 for jaw member 210 distally spaced-apart from pivot member 130. With respect to acting as a wire guide, body 172 of knife lockout 170 inhibits the lead wire 310 for jaw member 210 from interfering with and being damaged during the pivoting of shafts 110, 120 about pivot member 130, and inhibits the lead wire 310 for jaw member 210 from interfering with and being damaged by translation of knife 140.

Figures 5C, 5D:
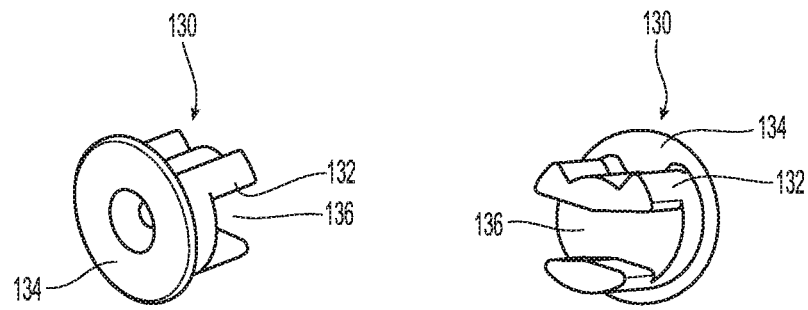
FIG. 5C is a first perspective view of a pivot member of the end effector assembly of the forceps of FIG. 1.
FIG. 5D is a second perspective view of the pivot member of the end effector assembly of the forceps of FIG. 1.

Referring also to FIGS. 5C-5D, pivot member 130 includes a body 132 and a cap 134. Body 132 of pivot member 130 is configured to extend through an aperture 125e defined through one of the side walls of distal clevis portion 125c of inner frame 124 of shaft 120, pivot aperture 115f of body plate 115a of inner frame 114 of shaft 110, and into a keyed aperture (or apertures) 125f defined through the other side wall of distal clevis portion 125c in fixed rotational orientation relative thereto. Body portion 132 of pivot member 130 is configured to be welded to the portion of the side wall of distal clevis portion 125c that surrounds keyed aperture(s) 125f. More specifically, the keying of body portion 132 within keyed aperture(s) 125f maintains proper orientation of pivot member 130 during welding. Body 132 is further configured to abut stop protrusion 115g (FIG. 3A) upon pivoting of shafts 110, 120 away from one another to define a furthest-spaced apart position of shafts 110, 120 and, similarly, a most-open position of jaw members 210, 220. A slot 136 defined through body 132 of pivot member 130 is configured to permit translation of knife 140 (FIGS. 9-10) therethrough, as detailed below.

Cap 134 of pivot member 130 defines a location recess 134' therein, as illustrated in FIG. 5C, for example, although other configurations are also contemplated. Location recess 134' is described below with respect to the assembly of forceps 100.

Turning to FIGS. 1 and 6-8, knife deployment mechanism 150 is coupled to shaft 110 and generally includes a pair of opposed triggers 152 extending from either side of shaft 110, a first linkage 154, a second linkage 156, and a biasing spring 158. Knife deployment mechanism 150 is disposed within outer housing 116 of shaft 110 with the exception of opposed triggers 152 which extend from either side of outer housing 116. First linkage 154 is configured for positioning on one side of inner frame 114 of shaft 110 and includes a pair of integral (or otherwise engaged) pivot bosses 161 extending from either side thereof at a first end portion of first linkage 154. One of the pivot bosses 161 extends through trigger aperture 115d of inner frame 114 (see FIG. 3A). Each pivot boss 161 extends through an aperture defined through outer housing 116 of shaft 110 to enable engagement of opposed triggers 152 therewith on either side of shaft 110, e.g., via press-fitting, adhesion, or other suitable engagement.

Figure 6:
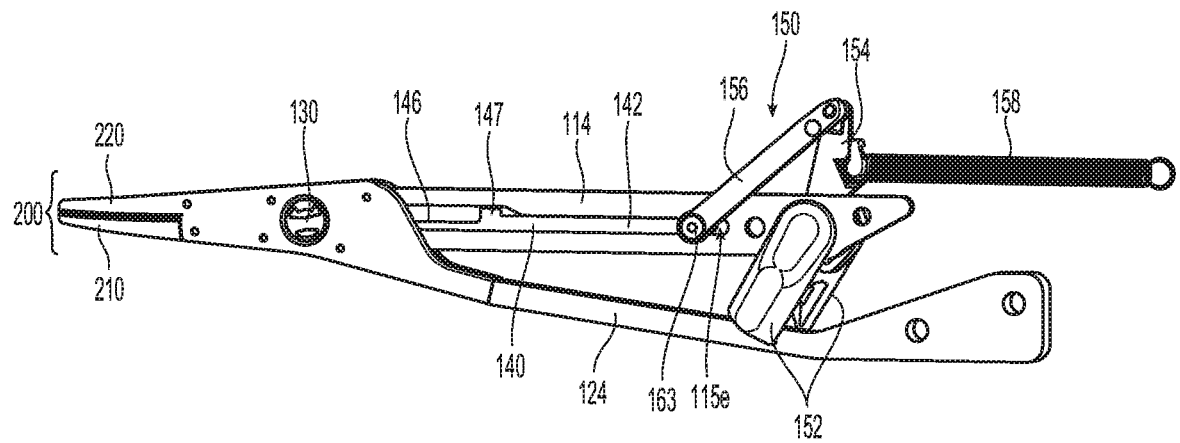
FIG. 6 is a side, perspective view of the forceps of FIG. 1 with portions removed to illustrate a knife deployment mechanism of the forceps.
Figure 7:
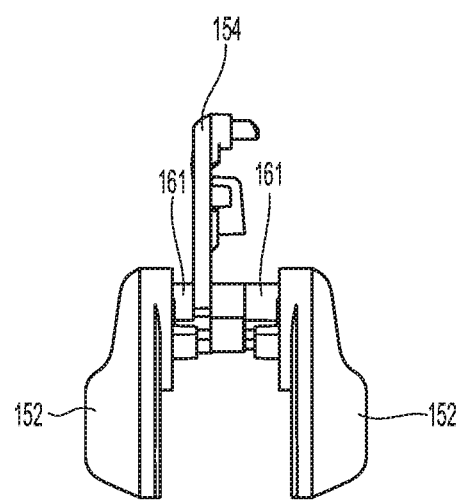
FIG. 7 is a rear view of a pair of triggers and a first linkage of the knife deployment mechanism of FIG. 6.
Figure 8:
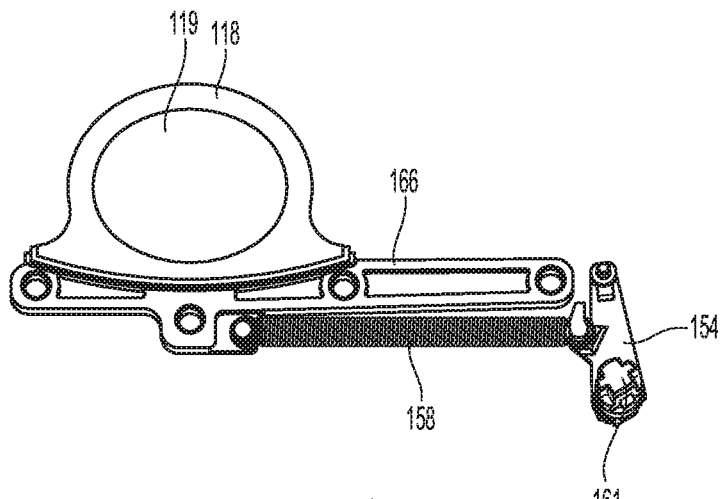
FIG. 8 is a side view of a handle of the first shaft of the forceps of FIG. 1 shown operably coupled to a first linkage of the knife deployment mechanism of FIG. 6.

Referring to FIGS. 6-8, a proximal end portion of second linkage 156 is pivotably coupled to first linkage 154 at a second end portion of first linkage 154. A distal end portion of second linkage 156 is pivotably coupled to knife 140 (see also FIGS. 9-10) via a pivot pin 163. Pivot pin 163 may be integrally formed with second linkage 156, e.g., as a post extending therefrom, or may be a separate component from second linkage 156. Pivot pin 163 extends transversely through longitudinal slot 115e of inner frame 114 of shaft 110 such that pivot pin 163 is constrained to longitudinal movement within longitudinal slot 115e. Second linkage 156 is disposed on one side of inner frame 114, which may be the same side as first linkage 154 or the opposite side (as shown). In either configuration, pivot pin 163 extends through second linkage 156 and through longitudinal slot 115e such that a portion of pivot pin 163 protrudes laterally from the opposite side of inner frame 114. While the knife deployment mechanism 150 embodied in FIGS. 6-8 is illustrated utilizing first and second linkages 154, 156, configurations utilizing greater or fewer linkages are also contemplated.

Biasing spring 158 may be configured as an extension spring or other suitable biasing spring 158. A distal end portion of biasing spring 158 is engaged to first linkage 154 and a proximal end portion of biasing spring 158 is engaged to a support plate 166. Support plate 166 includes handle 118 of shaft 110 integrally formed therewith or otherwise engaged thereto, and may be secured within outer housing 116 in any suitable fashion, e.g., via protrusion-aperture engagement. Support plate 166 provides increased structural support to shaft 110 to inhibit splaying of shafts 110, 120 during use. Shaft 120 similarly includes a support plate 168 integrally formed with or otherwise engaging handle 128 of shaft 120 and secured to outer housing 126, although support plate 168 need not extend distally as with support plate 166 (see FIGS. 2A and 2B).

Biasing spring 158 biases first linkage 154 towards a first orientation, corresponding to the un-actuated position of triggers 152 and the proximal-most position of second linkage 156, thereby biasing knife 140 towards a retracted position (e.g., a proximal-most position of knife 140). Upon rotation of either of triggers 152 relative to shaft 110, first linkage 154 is rotated against the bias of biasing spring 158 to thereby urge second linkage 156 distally such that pivot pin 163 is driven distally through longitudinal slot 115e to urge knife 140 from the retracted position towards an extended position, wherein knife 140 extends through slot 136 of pivot member 130, channel 115h of body plate 115a, and knife channels 215a, 225 of jaw members 210, 220 (FIGS. 3B and 4B, respectively).

Figure 9:
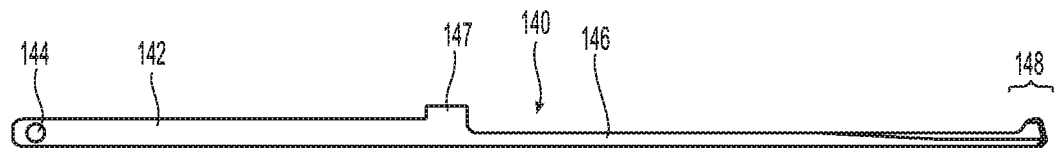
FIG. 9 is a side view of a knife of the forceps of FIG. 1.
Figure 10:
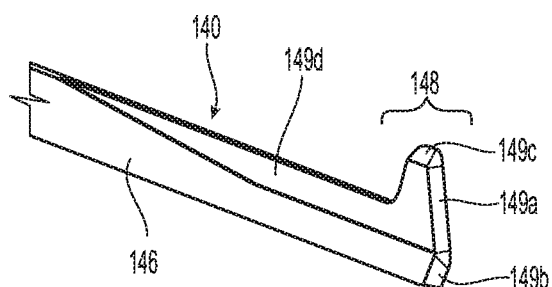
FIG. 10 is a perspective view of a distal portion of the knife of FIG. 9.

Referring to FIGS. 9 and 10, knife 140 includes a proximal body 142 defining an aperture 144 through which knife 140 is pivotably coupled to second linkage 156 of knife deployment mechanism 150 via pin 163 (see FIG. 6). Proximal body 142 of knife 140 is slidably disposed within channel 115h between body plate 115a and reinforcing plate 115b of inner frame 114 of shaft 110 (see FIG. 3A). Knife 140 further includes a distal body 146 defining a lower profile as compared to proximal body 142 and extending distally from proximal body 142. Distal body 146 defines a distal cutting portion 148. Distal cutting portion 148 defines an enlarged height as compared to distal body 146 and may be etched to define an asymmetrically sharpened configuration wherein one side of distal cutting portion 148 extends further distally than the opposite side (due to the removal of material from the opposite side during the etching process). The enlarged height of distal cutting portion 148 helps ensure that distal cutting portion 148 extends fully through the gap defined between jaw members 210, 220 (FIG. 1) and is at least partially received in respective knife channels 215a, 225 thereof (see FIGS. 3B and 4B). In the retracted position of knife 140, the enlarged height of distal cutting portion 148 is configured for receipt within a roof 213 defined by a proximally-extending portion of jaw support 212 of jaw member 210 (see FIG. 3A). The etched distal cutting edge of distal cutting portion 148 defines three segments: a main cutting segment 149a, a lower cutting segment 149b extending from one end of main cutting segment 149a at an angle relative thereto, and an upper cutting segment 149c extending from the opposite end of main cutting segment 149a at an angle relative thereto.

Knife 140 further includes a partial etch 149d extending along a portion of distal body 146 and distal cutting portion 148 of knife 140. Partial etch 149d may extend along either or both sides of knife 140. Partial etch 149d is configured to: inhibit wear of knife 140; promote flexibility of knife 140; facilitate translation of knife 140 through knife channels 215a, 225 of jaw members 210, 220 (see FIGS. 3A-4B); facilitate smooth translation of knife 140 through knife channels 215a, 225 (see FIGS. 3A-4B) should partial etch 149d come in contact with the sidewalls defining channels 215a, 225 (see FIGS. 3A-4B); and provide greater clearance between knife 140 and the sidewalls defining channels 215a, 225 (see FIGS. 3A-4B).

In use, distal body 146 of knife 140 is configured to reciprocate through slot 136 of pivot member 130 (FIG. 5D) to translate distal cutting edge 148 through knife channels 215a, 225 of jaw members 210, 220 in response to actuation of either trigger 152 (see FIGS. 2A-4B). Knife 140 further includes a stop shoulder 147 defined at the transition between proximal body 142 and distal body 146. Stop shoulder 147 defines a height greater than a height of slot 136 of pivot member 130 (FIG. 5D) such that stop shoulder 147 is inhibited from passing therethrough. Accordingly, stop shoulder 147 defines the distal-most extent of travel of knife 140, e.g., wherein stop shoulder 147 abuts pivot member 130 (FIG. 5D). Alternatively, rather than abutting pivot member 130, stop shoulder 147 may abut a portion of distal clevis portion 125c defining keyed aperture(s) 125f for similar purposes.

With momentary reference to FIGS. 1 and 2A, knife deployment mechanism 150 is operably positioned on shaft 110 and relative to shaft 120 such that triggers 152 do not extend beyond the height dimension of forceps 100 in the vicinity of triggers 152, even in the furthest-approximated position of shafts 110, 120. As a result of this configuration, forceps 100 benefits from a low-profile design that inhibits triggers 152 from catching on the surgeon, patient, or on nearby objections during use and/or as forceps 100 is inserted and withdrawn from the surgical site.

Turning to FIGS. 1, 2A, and 11A-11C, knife lockout 170 works in conjunction with shafts 110, 120 to prevent deployment of knife 140 prior to shafts 110, 120 reaching a sufficiently-approximated position corresponding to a sufficiently-closed position of jaw members 210, 220. Knife lockout 170 includes a body 172 (FIGS. 1-2B) that is disposed about a portion of the inner frame 114 of shaft 110 and forms a portion of outer housing 116 of shaft 110. More specifically, as shown in FIG. 1, body 172 of knife lockout 170 defines a complementarily-shaped abutting surface with the abutting surface of the adjacent other component(s) of housing 116 such that housing 116 defines a substantially continuous outer surface. Body 172 extends at least partially within U-shaped distal clevis portion 125c of shaft 110 to inhibit excess lateral play therebetween, as noted above.

Figure 11A:
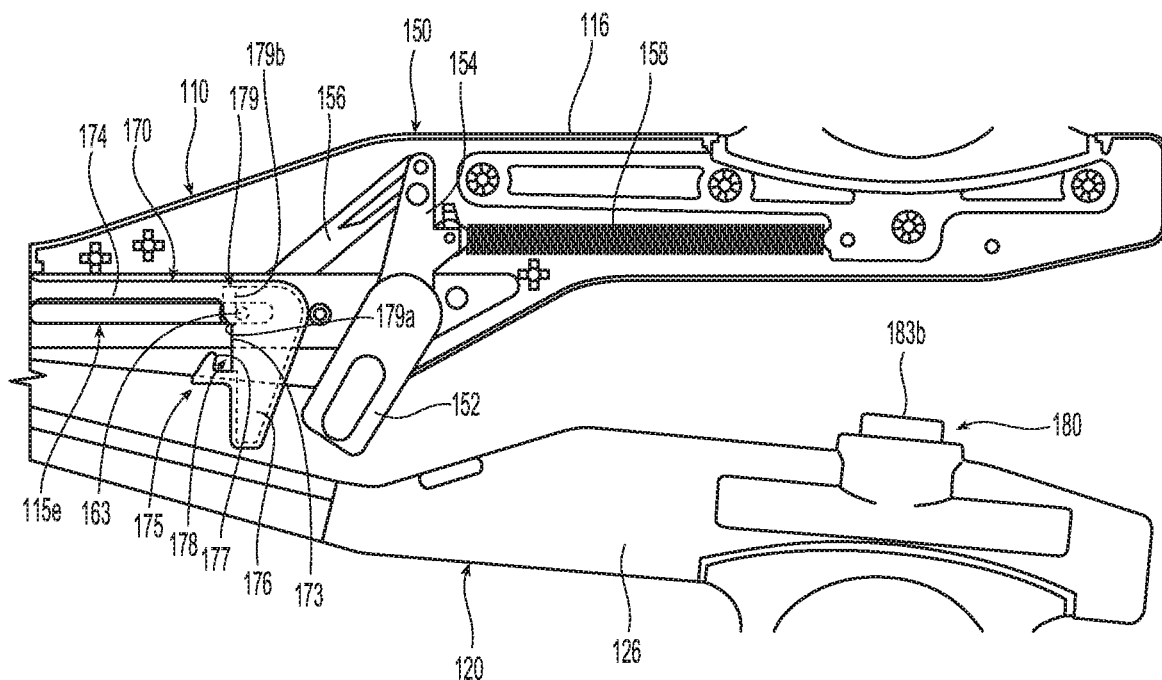
FIGS. 11A-11C are side views of a proximal portion of the forceps of FIG. 1 with portions removed to illustrate a knife lockout of the forceps.
Figure 11B:
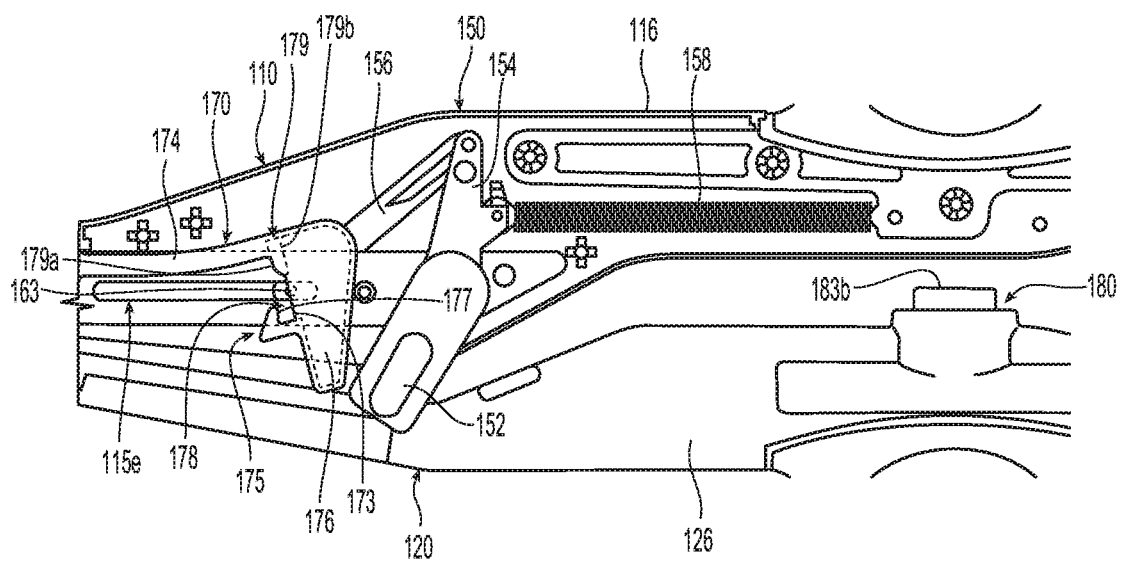
Figure 11C:
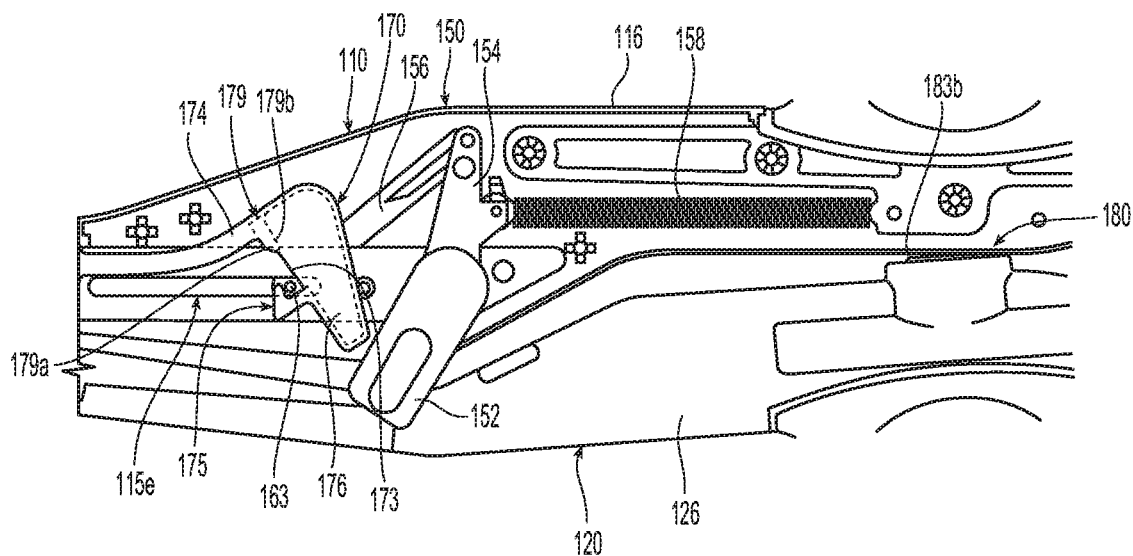

Referring to FIGS. 11A-11C, knife lockout 170 further includes a cantilever arm 174 extending proximally from body 172. Cantilever arm 174 and body 172 may be integrally formed, e.g., via injection molding, or may be attached in any other suitable fashion. Cantilever arm 174 extends along inner frame 114 of shaft 110 on an opposite side of inner frame 114 as compared to second linkage 156 of knife deployment mechanism 150. Cantilever arm 174 defines a relatively narrowed configuration to permit flexing of cantilever arm 174. A finger 176 integrally formed with cantilever arm 174 extends generally perpendicularly from a free end of cantilever arm 174 and through an opening defined in outer housing 116 of shaft 110 towards shaft 120. A first stop 179 is defined at the junction of cantilever arm 174 and finger 176. First stop 179 protrudes from cantilever arm 174 and defines an angled distal wall 179a and a vertical proximal wall 179b. The finger 176 includes a second stop 175 extending distally from a vertical distal wall 173 of finger 176. The second stop 175 defines a vertical proximal wall 177 that is generally parallel to vertical distal wall 173 of finger 176. A nook 178 is defined between vertical proximal wall 177 of second stop 175 and vertical distal wall 173 of finger 176.

Referring to FIG. 11A, with shafts 110, 120 sufficiently spaced-apart from one another and jaw members 210, 220 in the open position, finger 176 of knife lockout 170 is spaced-apart from outer housing 126 of shaft 120 such that cantilever arm 174 is disposed in an at-rest position. In its at-rest position, cantilever arm 174 extends along and in a generally parallel orientation relative to longitudinal slot 115e of inner frame 114 of shaft 110. Further, vertical proximal wall 179b of first stop 179 is disposed at the proximal end portion of longitudinal slot 115e and prevents distal advancement of pivot pin 163 through longitudinal slot 115e in the at-rest position of cantilever arm 174 and, accordingly, prevents deployment of knife 140.

Referring to FIG. 11B, in order to disengage knife lockout 170 to permit deployment of knife 140, shafts 110, 120 are sufficiently approximated such that jaw members 210, 220 are moved to the closed position (e.g., to grasp tissue therebetween) and a portion of outer housing 126 of shaft 120 contacts finger 176 of knife lockout 170 to urge finger 176 further into housing 116 of shaft 110. However, as shown in the configuration of FIG. 11B, shaft 110 is sufficiently spaced from shaft 120 such that outer housing 116 of shaft 110 is spaced from or otherwise out of engagement with depressible button 183b of switch assembly 180 such that depressible button 183b is not depressed to activate switch assembly 180 for initiating the supply of energy from the energy source (not shown) to jaw members 210, 220. As finger 176 is urged further into housing 116 of shaft 110, cantilever arm 174 is flexed such that vertical proximal wall 179b of first stop 179 is removed from the distal path of pivot pin 163. Once this has been achieved, knife deployment mechanism 150 may be actuated, as detailed above, to advance pivot pin 163 distally through slot 115e to move knife 140 from the retracted position towards the extended position.

Should shafts 110, 120 be moved apart from one another sufficiently such that shaft 120 no longer urges finger 176 to flex cantilever arm 174, cantilever arm 174 is resiliently returned to its at-rest position. If knife 140 is disposed in the retracted position at this point, vertical proximal wall 179b is returned to block the distal path of pivot pin 163. However, if knife 140 is disposed in the deployed position or a partially-deployed position, the return of cantilever arm 174 to its at-rest position does not block the distal path of pivot pin 163 via vertical proximal wall 179b. Rather, upon subsequent return of knife 140 to the retracted position, pivot pin 163 is moved proximally and into contact with angled distal wall 179a of first stop 179, camming therealong and urging cantilever arm 174 to flex from the at-rest position sufficiently so as to enable pivot pin 163 to return to the proximal end of longitudinal slot 115e. Once pivot pin 163 reaches this position, cantilever arm 174 is returned to the at-rest position and, as a result, vertical proximal wall 179b is returned to blocking the distal path of pivot pin 163, thereby resetting knife lockout 170 to prevent movement of knife 140 from the retracted position towards the extended position until shafts 110, 120 are once again sufficiently approximated. The biasing force of biasing member 158 is sufficient to move pivot pin 163 proximally to deflect cantilever arm 174 and reset knife lockout 170 as detailed above. As such, resetting of knife lockout 170 occurs automatically (if shafts 110, 120 are sufficiently spaced-apart) upon return of knife 140 to the retracted position.

Referring to FIG. 11C, to activate switch assembly 180 to initiate the supply of energy from the energy source (not shown) to jaw members 210, 220 for sealing tissue grasped between jaw members 210, 220, shafts 110, 120 are further approximated from the approximated position illustrated in FIG. 11B such that finger 176 is urged further into housing 116 of shaft 110 and depressible button 183b is engaged and depressed by a portion of outer housing 116 of shaft 110 to activate switch assembly 180. As finger 176 is urged further into housing 116 of shaft 110, cantilever arm 174 is further flexed such that vertical proximal wall 179b of first stop 179 remains removed from the distal path of pivot pin 163 and second stop 175 is urged further into housing 116 of shaft 110 such that the portion of pivot pin 163 that extends from second linkage 156 through longitudinal slot 115e is received within nook 178 of second stop 175. Once pivot pin 163 is received within nook 178, vertical proximal wall 177 of second stop 175 prevents distal advancement of pivot pin 163 through longitudinal slot 115e and, accordingly, prevents movement of knife 140 through jaw members 210, 220 during activation of switch assembly 180. In this manner, premature cutting of tissue during delivery of energy to tissue via jaw members 210, 220 (e.g., prior to completion of a tissue sealing cycle) is prevented.

Once a tissue sealing cycle is complete, switch assembly 180 may be deactivated by returning shafts 110, 120 to the approximated position illustrated in FIG. 11B such that jaw members 210, 220 remain in the closed position and depressible button 183b is no longer depressed by outer housing 116 of shaft 110. Upon returning to the approximated position illustrated in FIG. 11B, cantilever arm 174 remains sufficiently flexed such that vertical proximal wall 179b of first stop 179 is removed from the distal path of pivot pin 163. Accordingly, knife deployment mechanism 150 may be actuated, as detailed above, to advance pivot pin 163 distally through slot 115e to move knife 140 from the retracted position towards the extended position to cut tissue grasped between jaw members 210, 220 (e.g., subsequent to completion of sealing the grasped tissue). Following cutting of the grasped tissue, shafts 110, 120 may be moved apart from one another, as detailed above, to the spaced-apart position illustrated in FIG. 11A such that cantilever arm 174 is resiliently returned to its at-rest position to reset knife lockout 170 to prevent movement of knife 140 from the retracted position towards the extended position.

Figure 12A:
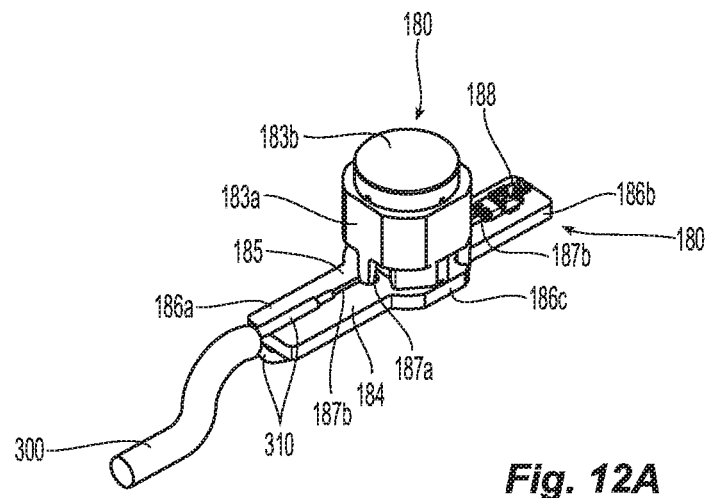
FIG. 12A is a top, perspective view of a switch assembly of the forceps of FIG. 1.
Figure 12B:
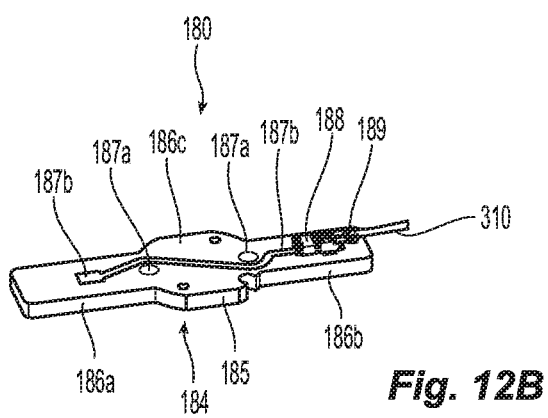
FIG. 12B is a bottom, perspective view of a circuit board of the switch assembly of FIG. 12A.

Turning to FIGS. 12A and 12B, switch assembly 180 is disposed on shaft 120 and generally includes a Printed Circuit Board (PCB) 184 and a button housing 183*a* supporting depressible activation button 183*b*. Depressible button 183*b* is configured to be contacted by the outer housing 116 of shaft 110 upon sufficient approximation of shafts 110, 120 so as to depress depressible button 183*b* and activate switch assembly 180. With additional reference to FIGS. 1-2B, as noted above, the position of shafts 110, 120 wherein switch assembly 180 is activated, together with the flexion of inner frame 124, enable application of a particular jaw force, or jaw force within a particular range, to tissue grasped between jaw members 210, 220.

PCB 184 of switch assembly 180 includes a board body 185 defining a first end portion 186*a*, a second end portion 186*b*, and a central portion 186*c*. Central portion 186*c* of board body 185 is configured to receive depressible activation button 183*b* thereon. More specifically, central portion 186*c* defines apertures 187*a* (or other suitable engagement features) to enable snap-fitting (or other suitable mechanical engagement) of depressible activation button 183*b* thereon. Central portion 186*c* further defines circuit traces 187*b* such that, upon mechanical engagement of depressible activation button 183*b* thereon, depressible activation button 183*b* is also electrically coupled to PCB 184. This configuration facilitates assembly and reduces the possibility of improper connections. Circuit traces 187*b* extend from central portion 186*c* towards first end portion 186*a* of board body 185 on both the upper and lower faces of board body 185 to enable connection of a pair of lead wires 310 (only one of which is shown) of electrosurgical cable 300 thereto, e.g., via soldering. Circuit traces 187*b* also extend from central portion 186*c* towards second end portion 186*b* of board body 185 on both the upper and lower faces of board body 185. A quick-connect receptacle 188 is disposed on each of the upper and lower faces of body board 185 towards second end portion 186*b* thereof in electrical communication with circuit traces 187*b*. Quick-connect receptacles 188 facilitate engagement of lead wire receptacles 189 (only one of which is shown) therewith, thus facilitating coupling of the lead wires 310 of jaw members 210, 220 with switch assembly 180. More specifically, lead wire receptacles 189 are configured to slide into snap fit or other suitable engagement with quick-connect receptacles 188 to both mechanically engage lead wire receptacles 189 with PCB 184 and electrically couple the lead wires 310 of jaw members 210, 220 to corresponding portions of circuit traces 187*b*. As a result of the above-detailed configuration of switch assembly 180, activation of depressible activation button 183*b* initiates the supply of energy from the energy source (not shown) to jaw members 210, 220 such that such energy may be conducted through tissue grasped between tissue-contacting surfaces 214, 224 of jaw members 210, 220 to treat tissue (see FIGS. 3A-4B).

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely controls the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:
1. An electrosurgical forceps, comprising:
first and second shafts each having a jaw member disposed at a distal end thereof, the shafts configured to move relative to each other to move the jaw members between an open position and a closed position;
a movable trigger coupled to one of the first or second shafts;

a knife operably coupled to the trigger via a linkage, the trigger configured to move the knife to cut tissue disposed between the jaw members; and a knife lockout defining a first stop and a second stop spaced from the first stop, the knife lockout configured to move between a first position, a second position, and a third position, wherein:

when the knife lockout is in the first position, the linkage contacts the first stop to prevent distal movement of the linkage and movement of the knife;

when the knife lockout is moved from the first position to the second position, the linkage is out of contact with the first stop such that movement of the knife is permitted; and when the knife lockout is moved from the second position to the third position, the linkage is received within a recess defined by the second stop to prevent distal movement of the linkage and movement of the knife.

2. The electrosurgical forceps according to claim 1, wherein when the knife lockout is in the first position, the jaw members are in the open position.

3. The electrosurgical forceps according to claim 1, wherein the jaw members are in the closed position when the knife lockout moves from the first position to the second position.

4. The electrosurgical forceps according to claim 1, wherein the jaw members are in the closed position when the knife lockout moves from the second position to the third position.

5. The electrosurgical forceps according to claim 1, further comprising a switch assembly disposed on one of the first or second shafts and configured to be engaged by the other of the first or second shafts to move the switch assembly between a deactivated position and an activated position to control delivery of electrosurgical energy to the jaw members.

6. The electrosurgical forceps according to claim 5, wherein the switch assembly is in the deactivated position when the knife lockout moves from the first position to the second position.

7. The electrosurgical forceps according to claim 5, wherein the switch assembly is in the activated position when the knife lockout moves from the second position to the third position.

8. The electrosurgical forceps according to claim 1, wherein the linkage includes a post extending therefrom configured to pivotably couple the linkage to the knife.

9. The electrosurgical forceps according to claim 8, wherein when the knife lockout is moved from the second position to the third position, the post is received within the recess defined by the second stop to prevent distal movement of the linkage and movement of the knife.

10. The electrosurgical forceps according to claim 1, wherein the knife lockout includes a flexible cantilever arm configured to be engaged by one of the first or second shafts to flex the cantilever arm to move the knife lockout between the first, second, and third positions.

11. An electrosurgical forceps, comprising:

first and second shafts each having a jaw member disposed at a distal end thereof, the shafts configured to move relative to each other to move the jaw members between an open position and a closed position;

a knife deployment mechanism coupled to one of the first or second shafts;

a knife operably coupled to the knife deployment mechanism via a pivot pin, the knife deployment mechanism configured to move the knife to cut tissue disposed between the jaw members; and a knife lockout defining a first stop and a second stop spaced from the first stop, the knife lockout configured to move between a first position, a second position, and a third position, wherein:

when the knife lockout is in the first position, the pivot pin contacts the first stop to prevent movement of the knife;

when the knife lockout is moved from the first position to the second position, the pivot pin is out of contact with the first stop such that movement of the knife is permitted; and when the knife lockout is moved from the second position to the third position, the pivot pin is received within a recess defined by the second stop to prevent movement of the knife.

12. The electrosurgical forceps according to claim 11, wherein when the knife lockout is in the first position, the jaw members are in the open position.

13. The electrosurgical forceps according to claim 11, wherein the jaw members are in the closed position when the knife lockout moves from the first position to the second position.

14. The electrosurgical forceps according to claim 11, wherein the jaw members are in the closed position when the knife lockout moves from the second position to the third position.

15. The electrosurgical forceps according to claim 11, further comprising a switch assembly disposed on one of the first or second shafts and configured to be engaged by the other of the first or second shafts to move the switch assembly between a deactivated position and an activated position to control delivery of electrosurgical energy to the jaw members.

16. The electrosurgical forceps according to claim 15, wherein the switch assembly is in the deactivated position when the knife lockout moves from the first position to the second position.

17. The electrosurgical forceps according to claim 15, wherein the switch assembly is in the activated position when the knife lockout moves from the second position to the third position.

18. The electrosurgical forceps according to claim 11, wherein the knife deployment mechanism includes:

a trigger extending from one of the first or second shafts;

a first linkage operably coupled to the trigger; and a second linkage having a first end portion pivotably coupled to the first linkage and a second end portion pivotably coupled to the knife via the pivot pin.

19. An electrosurgical forceps, comprising:

first and second shafts each having a jaw member disposed at a distal end thereof, the first and second shafts movable relative to each other to move the jaw members between an open position and a closed position;

a knife configured to move longitudinally to cut tissue disposed between the jaw members when the jaw member are in the closed position; and a knife lockout defining a first stop and a second stop spaced from the first stop, the knife lockout configured to move between a first position, a second position, and a third position, wherein:

when the knife lockout is in the first position, the first stop prevents movement of the knife;

when the knife lockout is moved from the first position to the second position, movement of the knife is permitted; and when the knife lockout is moved from the second position to the third position, a recess defined by the second stop prevents movement of the knife.

20. The electrosurgical forceps according to claim 19, wherein when the knife lockout is moved from the second position to the third position, a pivot pin coupled to the knife is received within the recess defined by the second stop to prevent movement of the knife.

* * * * *